United States Patent
Leavitt et al.

(10) Patent No.: US 10,994,034 B1
(45) Date of Patent: May 4, 2021

(54) APPARATUS FOR INACTIVATION OF AIRBORNE PATHOGENS AND PATHOGENS ON THE SURFACE OF AN OBJECT

(71) Applicant: MICRON PURE, LLC, Overland Park, KS (US)

(72) Inventors: David D. Leavitt, Shawnee, KS (US); John R. Bergida, Wildwood, MO (US); Devlin Leavitt, Shawnee, KS (US); Timothy B. Jackson, Chesterfield, MO (US)

(73) Assignee: MICRON PURE, LLC, Overland Park, KS (US)

( * ) Notice: Subject to any disclaimer, the term of this patent is extended or adjusted under 35 U.S.C. 154(b) by 0 days.

(21) Appl. No.: 16/988,270

(22) Filed: Aug. 7, 2020

Related U.S. Application Data

(60) Provisional application No. 63/019,522, filed on May 4, 2020, provisional application No. 63/003,344, filed
(Continued)

(51) Int. Cl.
*A61L 2/08* (2006.01)
*A61L 2/20* (2006.01)
(Continued)

(52) U.S. Cl.
CPC .............. *A61L 2/088* (2013.01); *A61L 2/202* (2013.01); *A61L 2/26* (2013.01); *A61L 9/205* (2013.01); *B01D 53/005* (2013.01); *B01D 53/02* (2013.01); *B01D 53/8675* (2013.01); *B01D 53/885* (2013.01); *A61L 2202/11* (2013.01); *A61L 2202/122* (2013.01); *A61L 2202/13* (2013.01); *A61L 2202/15* (2013.01); *A61L 2202/16* (2013.01); *B01D 2251/104* (2013.01); *B01D 2253/102* (2013.01);
(Continued)

(58) Field of Classification Search
CPC .......... A61L 2/088; A61L 2/202; A61L 9/205; B01D 53/02
See application file for complete search history.

(56) References Cited

U.S. PATENT DOCUMENTS

| 2005/0129571 A1* | 6/2005 | Centanni ................. A61L 2/208 422/31 |
| 2008/0213125 A1 | 9/2008 | Boast et al. |
| 2018/0250431 A1* | 9/2018 | Eide ..................... B01D 53/007 |

OTHER PUBLICATIONS

Muzhi, Ozone: A Powerful Weapon to Combat COVID-19 Outbreak, China.org.cn, http://www.china.org.cn/opinion/2020-02/26/content_75747237_4.htm, dated Feb. 26, 2020.
(Continued)

*Primary Examiner* — Kevin Joyner
(74) *Attorney, Agent, or Firm* — Lathrop GPM LLP

(57) ABSTRACT

An apparatus for the inactivation of airborne pathogens and pathogens on the surface of an object. The apparatus including a housing with an intake region and an exhaust region and an airflow path disposed between the intake and exhaust regions. The apparatus also includes a space within the housing for placement of the object as well as an intake fan and an oxidant generator proximate the intake fan. The apparatus includes an air filter disposed in the airflow path for removing particulates and pathogens and passes the intake air through either or both of an activated carbon filter and a catalyst to convert the oxidant into oxygen.

3 Claims, 10 Drawing Sheets

Related U.S. Application Data on Apr. 1, 2020, provisional application No. 62/994,397, filed on Mar. 25, 2020.

(51) Int. Cl.
 *A61L 9/20* (2006.01)
 *B01D 53/02* (2006.01)
 *B01D 53/88* (2006.01)
 *B01D 53/00* (2006.01)
 *B01D 53/86* (2006.01)
 *A61L 2/26* (2006.01)

(52) U.S. Cl.
 CPC .. *B01D 2255/2073* (2013.01); *B01D 2256/12* (2013.01); *B01D 2257/106* (2013.01); *B01D 2259/804* (2013.01); *B01D 2259/818* (2013.01)

(56) References Cited

OTHER PUBLICATIONS

Thailand Medical News, Ozone Can Be Used To Destroy The New Coronovirus and Disinfect Areas, https://www.thailandmedical.news/news/ozone-can-be-used-to-destroy-the-new-coronavirus-and-disinfect-areas, dated Feb. 5, 2020.

Hearn, Can Air Purifiers with MERV-13 Filter Protect You From the Coronavirus?, Digital Trends, Smart Home, https://www.digitaltrends.com/home/can-air-purifiers-protect-from-coronavirus/,. dated Jul. 10, 2020.

Hudson et al., Development of a Practical Method for Using Ozone Gas as a Virus Decontaminating Agent, Ozone: Science & Engineering, https://www.tandfonline.com/doi/full/10.1080/01919510902747969?src=recsys&, dated 2009.

Leusink, Cleaning with Liquid Ozone: What You Need to Know, Oxidation Technologies, LLC., https://www.oxidationtech.com/blog/cleaning-liqucleaning-with-liquid-ozone-what-you-need-to-knowid-ozone-need-know/, dated May 31, 2016.

Three Bond Technical News, Titanium-Oxide Photocatalyst, Issued Jan. 1, 2004.

\* cited by examiner

US 10,994,034 B1

APPARATUS FOR INACTIVATION OF AIRBORNE PATHOGENS AND PATHOGENS ON THE SURFACE OF AN OBJECT

RELATED APPLICATION

This application claims priority from U.S. Provisional Application Nos. 62/994,397 filed Mar. 25, 2020, 63/003,344 filed Apr. 1, 2020 and 63/019,522 filed May 4, 2020.

FIELD OF USE

This disclosure is directed to an apparatus for inactivating pathogens such as, but not exclusively, coronaviruses.

BACKGROUND

Disease can spread when people with certain infections cough, sneeze, or talk, spewing nasal and throat secretions into the air. Some viruses or bacteria take flight and hang in the air or land on people or surfaces. When a person breathes in airborne pathogenic organisms, they take up residence inside the person creating a wide range of symptoms. Unsuspecting individuals can also pick up germs when airborne pathogens come to rest on a surface and the person then touches the surface that harbors them. Once the person touches the surface, they often touch their own eyes, nose, or mouth leading to infection of the individual.

Some pathogens are also suspended in biofluids such as blood, mucus, saliva, vomit, liquid feces and related secretions. These contaminated biofluids not only encounter the surfaces of objects and materials but can be transported into the sub-surfaces by capillary forces when the fluids are absorbed through the pores found in porous objects and materials. Pathogens that are resident in sub-surfaces may be shielded from inactivation by chemical disinfectants such as alcohol, hydrogen peroxide and ultraviolet light sterilization processes that are commonly used to inactivate pathogens in the air and on the surface of objects.

Pathogens found in sub-surface pores are protected from inactivation when methods that are only effective for surface treatment are used and often migrate to the surface after such treatment to re-colonize the surfaces, leading to infection of individuals who then encounter the pathogens when they contact the surfaces. Air flowing across the surfaces of previously treated materials containing contaminated biofluids within their sub-surface facilitates the wicking of contaminated biofluids to the surface. The pathogens in the transported biofluids often become airborne after the biofluid in which they were suspended dehydrates in contact with air blowing across the surfaces.

Pathogens that are airborne or are found on the surfaces and within the surfaces of objects and materials create various symptoms that in extreme cases can lead to death, particularly in individuals with compromised immune systems. The common cold is usually caused by a rhinovirus. Influenza consists of many strains and is constantly changing, making it very difficult for the body to develop an immunity. Chickenpox is caused by the varicella-zoster virus and can be spread for a day or two before the infected individual displays the telltale rash. It can take up to 21 days after exposure for the disease to develop.

Mumps is another very contagious disease, particularly in crowded conditions. Mumps can be spread before symptoms appear and for up to 5 days after. Mumps was quite common in the United States, but rates have declined by 99 percent due to vaccination. Measles is a very contagious disease, particularly in crowded conditions. The virus that causes measles can remain active in the air or on surfaces for up to 2 hours. Measles can be transmitted to others up to 4 days before and 4 days after the measles rash appears. Measles is a leading cause of death among children worldwide and was responsible for 140,000 deaths in 2018. It's estimated that the measles vaccine prevented around 23 million deaths from 2000 to 2018.

Whooping cough is a respiratory illness that causes swelling of the airways that results in a persistent hacking cough. Whooping cough is at the height of contagiousness for about 2 weeks after the coughing starts. Worldwide, there are about 24.1 million cases of whooping cough every year, resulting in 160,700 deaths. In 2018 there were 15,609 reported cases of whooping cough.

Tuberculosis is an airborne disease. This is a bacterial infection that does not spread easily and a person generally must to be in close contact with another person who has it for a long time. Tuberculosis can be contracted without becoming ill or transmitting it to others. About 1.4 billion people worldwide have tuberculosis and most are not sick. About 10 million people worldwide have active tuberculosis.

The rapidly spreading coronavirus, SARS-CoV-2, and the disease it causes, COVID-19, continue to cause widespread concern as of early 2020. The most common symptoms of COVID-19 include fever, cough, fatigue, and shortness of breath. Coronaviruses are enveloped viruses and are easier to inactivate than non-enveloped viruses. To inactivate or attenuate a pathogen such as a virus means to cause the pathogen to lose disease producing capacity. To inactivate an enveloped virus an appropriate disinfectant product must be utilized.

Viruses that are airborne or that remain on surfaces and within the sub-surfaces of objects and materials create a substantial public health risk that can be lessened by the utilization of an apparatus as disclosed herein. Specifically, the disclosed apparatus for inactivation of such pathogens is capable of scrubbing from airflow particulates as small as 0.3 microns. Researchers have determined that larger inert particulates are often colonized by viruses that may only be 0.10 to 0.15 microns in major dimension. Consequently, there are significant health related benefits to removing larger particulates from airborne circulation.

Devices such as air purifiers or air ionizers are often employed to reduce the amounts of pathogens in air by exposing them to oxidants such as reactive oxygen species (ROS). Such ROS include hydrogen peroxide ($H_2O_2$), superoxide ($°O_2^-$), hydroxyl radicals ($OH°$), singlet oxygen ($O=O$ or $^1O_2$), alpha-oxygen ($\alpha O$), atomic oxygen ($°O$) and ozone. ROS can be categorized as radicals and non-radicals. Radical ROS include superoxide, hydroxyl radicals and atomic oxygen. Non-radical ROS include hydrogen peroxide, ozone, and singlet oxygen. Most ROS are gases at standard temperature and pressure except hydrogen peroxide, which is a liquid. In many air purifiers or ionizers, a corona discharge generator is used to produce the ROS ozone. Studies have shown that concentrations of ozone of approximately 100 ppm are considered highly effective for inactivating pathogens in air with exposure times of as little as 10 to 15 minutes.

Lower ozone concentrations in the range of 20-25 ppm are also effective, although in the case of lower concentrations additional exposure time is required to inactivate the pathogens. Unfortunately, devices such as these often generate insufficient amounts of ozone to be effective as a disinfectant or can potentially release excess ozone into an environment in which people and animals respire when not equipped with an effective ozone destruction device to treat the exhaust gas. High levels of ozone can cause pulmonary irritation and studies have revealed that maximum safe levels of respired ozone are from 50 ppb to 100 ppb for an eight-hour exposure.

Air purifiers or ionizers also utilize devices that produce ultraviolet light to inactivate pathogens in air and on surfaces. Ultraviolet light has a wavelength spectrum from 100 to 400 nm and is subdivided into four regions: UVA (320 to 400 nm), UVB (280 to 320 nm), UVC (200 to 280 nm) and short wavelength ultraviolet light below 200 nm. UVC has the strongest germicidal effect and is widely used in the form of mercury lamps to inactivate pathogens. Ultraviolet light can also be used to produce ROS when exposed to air while in contact with a photocatalyst such as titanium dioxide, $TiO_2$. Short wavelength ultraviolet light having wavelengths less than 200 nm and preferably around 185 nm is most effective to produce ROS such as ozone and hydroxyl radicals using a photocatalyst. Paradoxically, ultraviolet light having wavelengths between 240-315 nm, preferably around 254 nm, can be used to decompose the ROS ozone into oxygen. Thus, the proper selection of the wavelength emitted by an ultraviolet light emitting source is a critical factor in the design of an effective pathogen destruction device.

Reports of the effectiveness of air purifiers or ionizers are typically based upon the inactivation of airborne pathogens, not pathogens that are embedded in biofilms or within the sub-surfaces of objects and materials. The reaction time for inactivation of pathogens by oxidants or ROS is very fast in air but much slower in fluids. In biofluids the rate of inactivation is governed by the first principles of oxidant concentration and diffusion through the media. Although oxidant concentrations of approximately 100 ppm are considered highly effective for inactivating pathogens with exposure times of as little as 10 to 15 minutes when the pathogens are airborne, much longer exposure times are required at these oxidant concentrations to effectively treat pathogens found in biofilms and sub-surface pores because of the time required for the oxidants to diffuse through the biofilms and sub-surface pores in order to make contact with the pathogens within them. The diffusion of an oxidant is similar to the diffusion of oxygen through a biofilm or subsurface pores, and studies have shown that the rate of diffusion of such gases through such materials follow first order kinetics. As shown by the following equation, the rate of diffusion of an oxidant is proportional to the concentration of the oxidant:

$$\text{Rate of diffusion}=k[A]$$

where k is a constant and [A] is the concentration of the oxidant.

Because the rate of pathogen inactivation is proportional to the amount of oxidant in contact with the pathogen and the rate of diffusion of the oxidant through biofilms and sub-surface pores is proportional the concentration of the oxidant available to diffuse, the rate of inactivation of a pathogen can be seen to increase by increasing the concentration of the oxidant. Consequentially, the residence time for effective inactivation of pathogens in biofilms and subsurface pores can be seen to be greatly reduced by operating a pathogen inactivation apparatus at much higher oxidant concentration than is typically used to inactivate pathogens in air.

Oxidant concentration in the space surrounding a pathogen is achieved by transferring the oxidant into the surrounding space from a concentrated source of the oxidant such as from a pressurized canister of concentrated oxidant or by the production of the oxidant in situ by a chemical or photochemical reaction. Because gaseous ROS are very reactive, unstable, and have a short half-life, it isn't practical to store them in containers typically used for storing liquid oxidants such as hypochlorite or hydrogen peroxide. These oxidants are preferably generated at the time of their use or application. For example, a corona discharge generator produces ozone when an electrical discharge splits a stable oxygen molecule into two oxygen radicals (O°), which then collide with a separate molecule of oxygen ($O_2$) as shown in the following formula:

$$O_2+O°\rightarrow O_3$$

Here rate of formation of ozone follows second order kinetics. As shown by the following equation, the rate of formation of ozone is dependent on how much of each of the reactants is present.

$$\text{Rate of ozone production}=k[O_2][O°]$$

where k is a constant and $[O_2]$ is the concentration of oxygen and

[O°] is the concentration of oxygen atoms.

From the above equation it is evident that the rate of production of ozone increases in proportion to an increase in the concentration of oxygen. This relationship is also found for another ROS. Consequentially, increasing the oxygen concentration in the air will cause an increase in the production of ROS generated by means of ROS generating devices that produce ROS from oxygen and result in a reduction in the time for effective inactivation by exposure to ROS of pathogens in biofilms and subsurface pores.

There exists a tremendous need for an apparatus or system to "inactivate" or "attenuate" pathogens and particularly viruses that are present in air and on the surfaces and within the sub-surfaces of objects and materials in a safe and effective manner. To render a very high percentage, if not all such pathogens inactive, is the ultimate objective of the apparatus disclosed herein.

SUMMARY

The apparatus and system disclosed herein is directed to the inactivation, or attenuation, of pathogens that are present in air and on the surfaces and within the sub-surfaces of objects and materials. The apparatus, in a first embodiment as disclosed herein, is a housing capable of being heated and pressurized with air in the presence of ultraviolet light and ROS.

The apparatus operates in two phases, a pathogen inactivation phase and a ROS decomposition phase. During the pathogen inactivation phase, the apparatus optimizes the flow of a mixture of air and both radical and non-radical ROS with heat and pressure to induce the penetration of these ROS into and within the sub-surfaces of the materials to be decontaminated and to facilitate the wicking of the contaminated biofluids from the sub-surfaces to the surfaces of the materials where inactivation of the pathogens by the ROS and ultraviolet light is enhanced. During the ROS decomposition phase, the apparatus safely and effectively removes residual ROS and any particulate material from the housing before the housing is depressurized and opened to remove the decontaminated objects and materials.

The apparatus as disclosed herein may be sized to accommodate smaller housings useful for decontaminating medical equipment, respirators, masks, and clothing, or for much larger housings such as a shipping container to inactivate pathogens on large packages and bulk quantities of smaller packages. Ideally the apparatus, depending upon initial design criteria, can be manually ported to various locations such as residences, commercial buildings, hospitals, warehouses, rail cars or truck-trailers to facilitate convenient disinfection of received shipments of goods and materials, or to areas in a facility where contaminated materials such as medical wastes are staged prior to final disposal.

Before the start of the pathogen inactivation phase, the door to the apparatus is opened and the object to be disinfected is placed on a shelf. The shelf has small holes to allow for air and ROS to pass through while supporting the object to be disinfected. After the object is placed on the shelf, the door is then closed and locked. Once the door is closed, the pathogen inactivation phase can begin.

To start the pathogen inactivation phase, the compressor is switched on, filling the housing cavity with air. As the compressor switches on, air enters the compressor and a throttle valve, located after a HEPA filter but before an activated carbon filter, is closed. The throttle valve is closed to keep air from escaping through the activated carbon filter, the ozone decomposition catalyst, and out the exhaust vent while the housing cavity is being pressurized. The compressor continues to pressurize the air within the housing cavity until a desired pressure is reached, typically around 1.5 atm. The volume of the housing is held constant to allow the pressure and moles of air within to increase proportionately.

The housing may be fabricated in essentially an unlimited number of shapes, sizes and materials based upon the particular needs of the end-user. Examples include smaller home devices for groceries, mail, shoes, headwear, masks, gloves, keys, purses, hand bags, backpacks, and electronics as well as larger industrial devices built into or attachable to shipping containers, trucks, cabinets, storage units, or conveyer systems. Even ornamental configurations of the apparatus are contemplated by this disclosure. For example, in a residence the apparatus may be fabricated into a decorative mail box for receiving mail, packages and delivered items where these items are placed within the apparatus, the lid secured to seal the unit and the device activated to expose the items within to the optimum mixture of pressurized air and oxidant in contact with ultraviolet light and heat for a set amount of time necessary to inactivate all the pathogens. In a constant volume housing the mass of air will increase in proportion to the increase in pressure as the air compressor pumps air into the housing, as shown in Table 1.

with biofluid to facilitate the wicking of the fluid out of the sub-surface pores and to vaporize some of the water in the biofluids.

As the air within the housing is heated, the biofluids migrate from the sub-surfaces and pores in the objects and materials to the surfaces in response to the increase in temperature and capillary forces. Some of the liquid water in the biofluids is converted to water vapor which increases the humidity of the air within the housing. The period for heating the air and the desired increase in temperature of the contents within the housing is specifically selected for the materials and objects to be treated by the apparatus.

Once the housing cavity is heated to the desired temperature, the heater is switched off. The housing cavity has now been pressurized and heated so that any ROS produced will be in an environment most conducive to inactivating pathogens. Two types of ROS generators are contemplated to be employed by the apparatus to produce a variety of ROS. One type, a corona discharge generator, predominately produces ozone as a final product, although other ROS are also produced in smaller amounts. The other type is an ultraviolet light source emitting 185 nm wavelength light in contact with a photocatalyst which produces a mixture of ozone, superoxide, and hydroxyl radicals.

A photocatalyst such as titanium dioxide, $TiO_2$, is coated along the walls of the housing. As the ultraviolet light at a wavelength of 185 nm contacts the photocatalyst, the mixture of ozone, superoxide, and hydroxyl radicals is produced. A set of nozzles above the catalyst coated areas intermittently release small bursts of water vapor into the housing cavity to ensure that the environment is at the proper humidity to maximize the photocatalyst production of ROS. At this point, the fan distributes the airstream comprising a mixture of air, ROS, water vapor, and particulates within the housing to induce turbulent mixing of the airstream around the baffles, materials, and objects within the housing.

The longer the pathogens stays in the contact with the ROS, undergoing turbulent flow and exposure to ROS and the ultraviolet radiation light, the greater is the pathogen inactivation rate. The time for contacting the contents within the housing with the mixture of air and ROS is specifically selected for the materials and objects to be treated by the apparatus.

Once the desired time has elapsed, the pathogen inactivation phase has ended, and the ROS decomposition phase begins. During this phase, the fan continues to circulate the airstream and the heater is switched on at a temperature

TABLE 1

| HOUSING - DIMENSIONS FT | PRESSURE ATM | TEMPERATURE K | HOUSING - VOLUME L | MOLES AIR | MOLES O2 | GRAMS O2 |
| --- | --- | --- | --- | --- | --- | --- |
| 6' × 3' × 4' | 1 | 273 | 2039 | 91.01 | 19.06 | 610.0 |
| 6' × 3' × 4' | 1 | 298 | 2039 | 83.38 | 17.46 | 558.8 |
| 6' × 3' × 4' | 2 | 298 | 2039 | 166.75 | 34.93 | 1117.7 |
| 6' × 3' × 4' | 3 | 298 | 2039 | 250.13 | 52.39 | 1676.5 |
| 6' × 3' × 4' | 4 | 298 | 2039 | 333.50 | 69.86 | 2235.4 |

The air within the housing cavity is pressurized to force air into the sub-surfaces of the materials and objects to be disinfected. Once the desired pressure is reached, the compressor is switched off and a heater is switched on. The heater is used to heat the air to a maximum of 100° C. but at a preferred temperature less than 50° C. At the same time, a fan is also switched on to circulate the heated airstream in contact with the objects and materials that are contaminated between 50° C. and 100° C. A second ultraviolet light emitting source having wavelengths between 240-315 nm and preferably at 254 nm is also switched on to facilitate further decomposition of ozone. The second ultraviolet light emitting source also provides an additional benefit in that such wavelengths emitted are within the UVC spectrum and have a strong germicidal effect even in environments free of ROS.

The provision for the use of a second ultraviolet light emitting source thus provides two functions; to decompose excess ROS remaining and continue to inactivate pathogens that may have survived the previous phase. As the airstream is exposed to the combination of heat at a temperature above 50° C. and the selected wavelengths of ultraviolet radiation light, the ozone in the airstream begins to rapidly decompose into oxygen and water vapor.

After a period optimized for the decomposition of ozone, the heater and the ultraviolet light emitting source are switched off and the throttle valve is engaged. The airstream then passes through the HEPA filter into an activated carbon filter that reacts with the ozone to produce oxygen, carbon dioxide and water vapor. The airstream continues to pass through activated carbon filter into the ozone destruction catalyst, which completes the conversion of ozone into oxygen. With the fan still engaged, the compressor is started to draw fresh air from the environment to sweep through the housing and flow through the HEPA filter, the fully open throttle valve, the activated carbon filter and the ozone destruction catalyst for a set period. The fan is then switched off and the housing opened so that the disinfected objects and materials can be removed.

It is critical that the pathogens be exposed to the ROS for sufficient time and at a sufficient pressure to diffuse the ROS through the surface pores and into the sub-surfaces of the materials and objects where the absorbed biofluids containing the pathogens reside at an ROS concentration that is high enough to allow the ROS to adequately inactivate the pathogens.

It is also critical that the ROS, materials and objects are heated to a sufficient temperature for a sufficient time during the pathogen inactivation stage of the process to facilitate the wicking of the biofluids containing pathogens from within the subsurface pores to the surfaces of the materials and objects in the housing in order to maximize the interaction of the ROS with the pathogens.

It is also critical that the ROS, materials and objects are heated to a sufficient temperature for a sufficient time during the ozone decomposition stage to facilitate the thermal decomposition of any excess ROS remaining in the air being discharged from the disclosure at the area for exhausting air.

It is also critical that the ROS, materials and objects are exposed to an ultraviolet light emitting source having a wavelength between 240-315 nm for a sufficient time during the ROS decomposition stage to facilitate the decomposition of any excess ROS remaining in the air being discharged from the disclosure at the area for exhausting air.

It is also critical that the airstream exiting the housing that contains any residual ozone be treated to remove the ozone by means of an ozone destruction catalyst for a sufficient time during the ROS decomposition stage to facilitate the decomposition of any excess ozone remaining in the air being discharged from the air exhaust.

It is an object of the apparatus disclosed herein to inactivate a high percentage of the pathogens in air or on the surfaces and within the sub-surfaces of objects and materials prior to discharging the exhausted air into the occupied space.

It is a further object of the apparatus as disclosed herein to be able to scale the apparatus to inactivate pathogens in housings of any dimension.

It is a further object of the apparatus as disclosed herein to deliver an effective dose of ROS to contact essentially 100% of the surfaces and subsurface void space areas where pathogens may be found on the particles, objects and materials within the housing of the apparatus.

BRIEF DESCRIPTION OF THE DRAWINGS

Illustrative embodiments of the apparatus disclosed herein are described in detail below with reference to the attached figures, which are incorporated by reference herein and wherein.

DETAILED DESCRIPTION

The apparatus and system disclosed herein is directed to the inactivation or attenuation of pathogens that are present in air and on the surfaces and within the sub-surfaces of objects and materials. The apparatus as disclosed herein operates in two phases, a pathogen inactivation phase and a reactive oxygen species ("ROS") decomposition phase.

Figure 1:
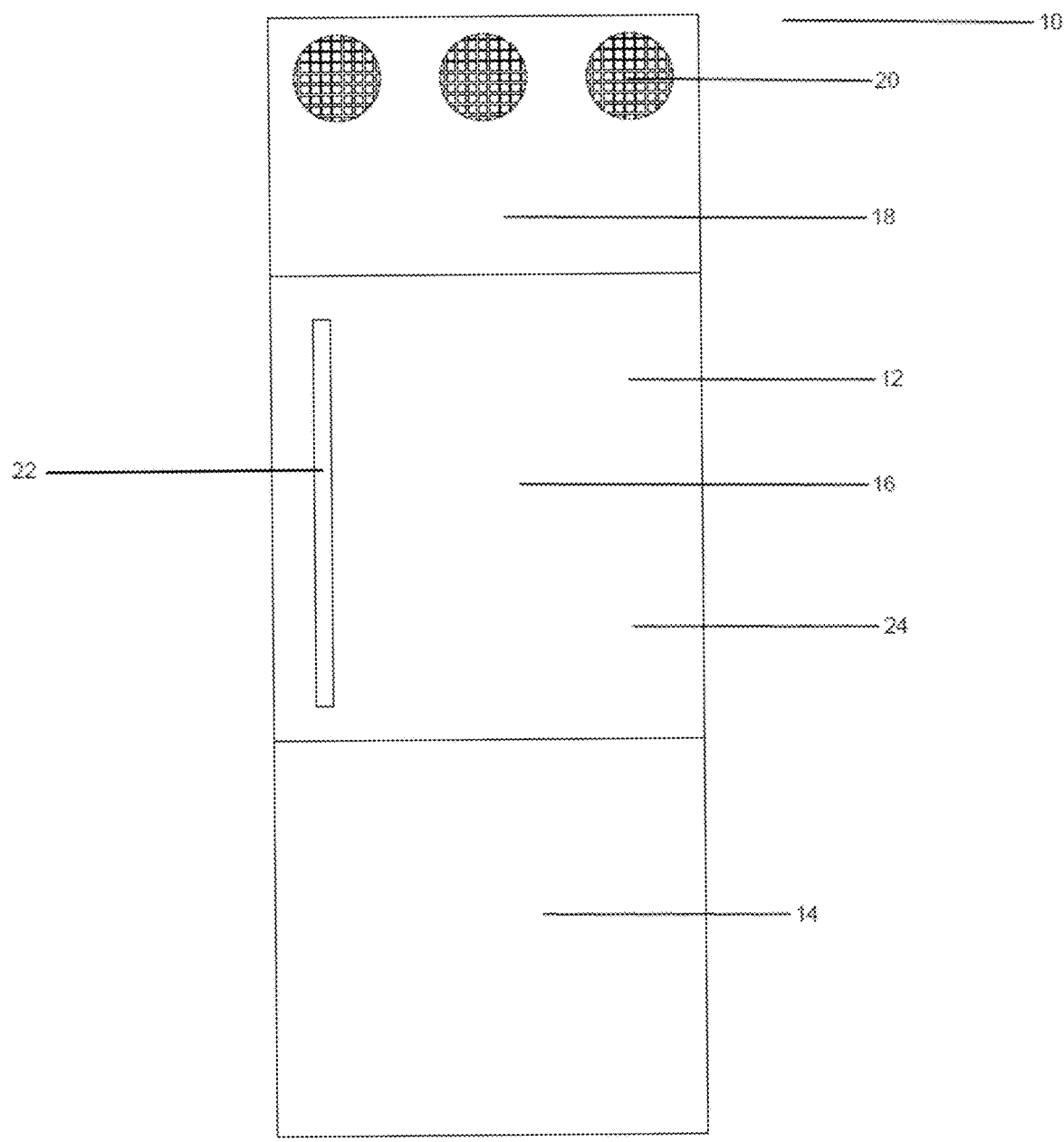
FIG. 1 illustrates an elevation view of an embodiment of the exterior of a housing for the apparatus for inactivation of airborne pathogens.
Figure 2:
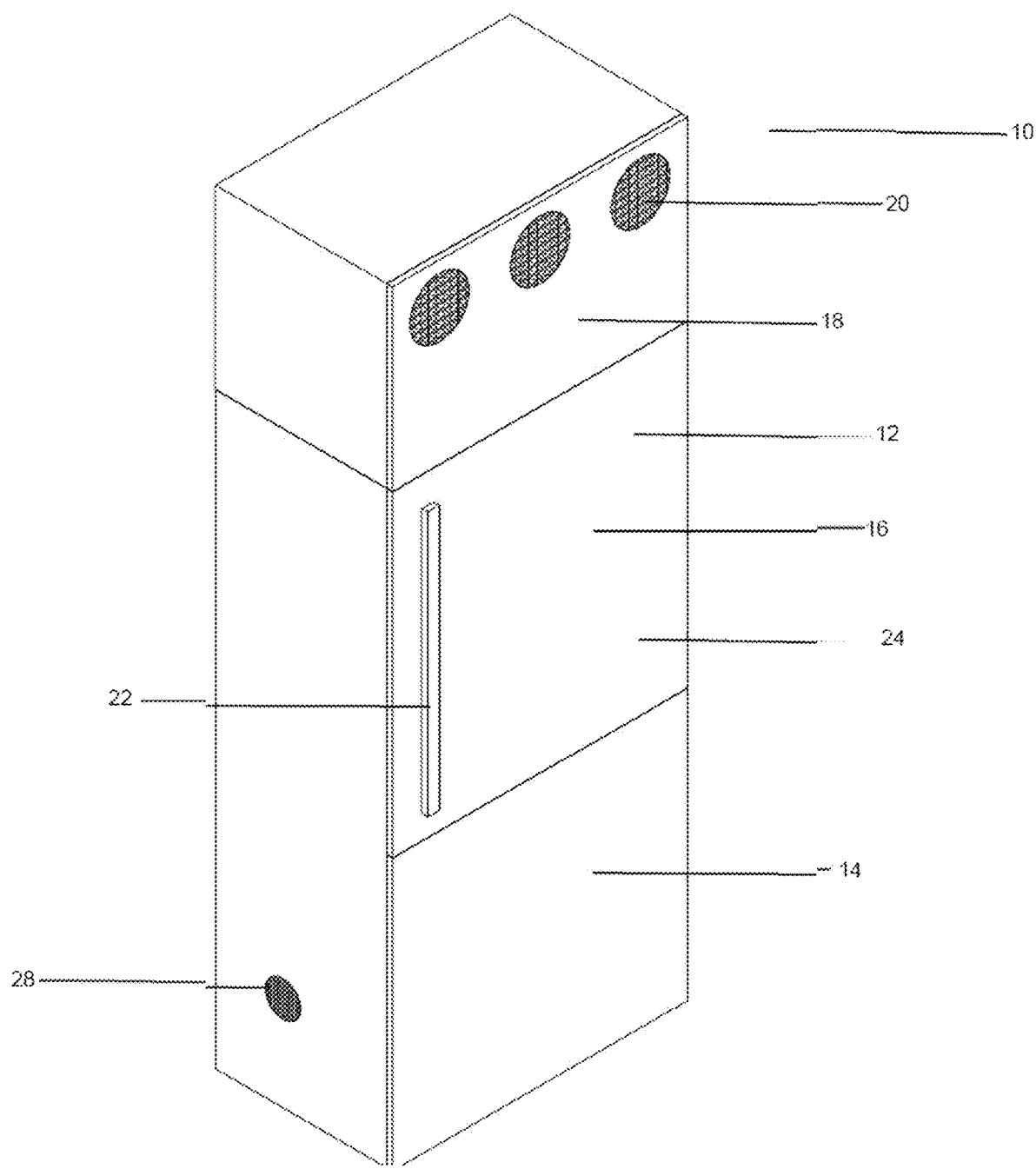
FIG. 2 illustrates a perspective view of an embodiment of the outside housing for the apparatus for inactivation of airborne pathogens.

As seen in FIGS. 1 and 2, the apparatus 10 as disclosed herein consists of a housing 12 with three main sections, a bottom 14, a middle 16, and a top 18. The top section contains three exhaust vents 20 that release the highly filtered air into the environment upon completion of the pathogen inactivation process. The middle section 16 contains a handle 22 on a hinged door 24 that is used at the start of the pathogen inactivation phase to open the middle section 16 and allow for objects or materials to be placed upon a shelf. Once the objects or materials are placed on the shelf, the door 24 to the middle section 16 is closed using the handle 22, in preparation for pressurizing the housing 12.

Figure 3:
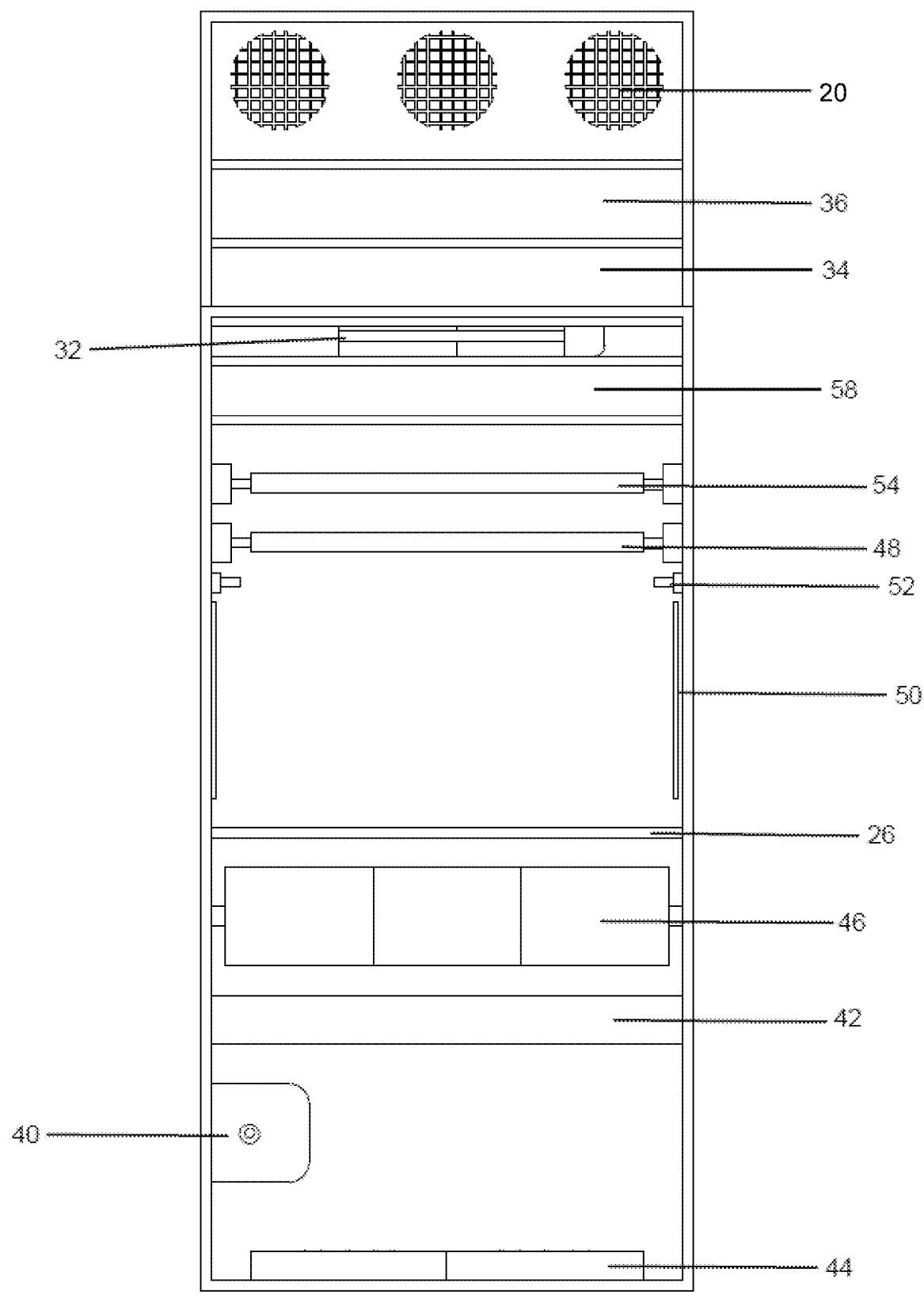
FIG. 3 illustrates a front view of an embodiment of the internal components for the apparatus for inactivation of airborne pathogens.

In the embodiment of the apparatus for inactivation of airborne pathogens shown in FIG. 3, the apparatus contained five corona discharge ozone generators each capable of producing 10 grams of ozone/hour under standard conditions of 1 atm pressure and a temperature of 298° K (25 C).

When the apparatus was operated within an enclosure having a volume of 16,000 liters, the ozone generators operating at a flow rate of 160 cubic feet per minute produced 50,000 mg of ozone per hour or 833 mg ozone per minute which is equivalent to a total ozone concentration of 3,125 mg/m$^3$ or 1,460 ppm within the enclosed space during 1 hour of operation.

When the apparatus is operated at 2 atm pressure with two times the initial concentration of oxygen and with supplemental oxidant production from Ultraviolet radiation in contact with a photochemical catalyst, the production of oxidant will increase proportionately according to the rate equation shown herein. The resulting oxidant concentration attained within the housing charged with oxygen at 2 atm pressure under these conditions will be significantly greater than 20 times the concentration shown by studies to be effective at inactivating pathogens in air and is more than adequate to inactivate pathogens in biofilms and subsurface pores.

When the air containing the excess oxidant was discharged to the environment by passing into contact with the HEPA filter, the activated carbon filter and the fixture containing the ozone destruction catalyst within the apparatus, the ozone concentration in the exhaust gas stream was reduced to less than 13 ppb and thus complied with the threshold standard of 50 ppb ozone in air.

Once the desired pressure is reached, the compressor 40 is switched off and a heater 42 is switched on. The heater is used to heat the air to a temperature less than 100° C., but typically less than 50° C. A fan 44 is turned on at the same time as the heater 42 to circulate the air and facilitate contact of the heated airstream with objects and materials that are contaminated with pathogens. When contacted with the heated airstream, biofluids that may be contained within the sub-surfaces of the objects or materials will be induced to move out of the sub-surfaces and to the surfaces of the objects or materials. At this point, water will vaporize out of the biofluids on the surfaces.

Once the housing cavity is heated to the desired temperature, the heater 42 is switched off, and the fan 44 continues to run. The housing cavity has now been pressurized and heated that any ROS produced will be in an environment most conducive to inactivating pathogens. At this point, the corona discharge generator 46 is switched on, producing predominantly ozone, with a small amount of another ROS.

As the corona discharge generator 46 is switched on, the ultraviolet light source emitting 185 nm wavelength light 48 is also switched on. As the ultraviolet light of 185 nm wavelength is created, the light travels throughout the housing cavity, reaching an area coated with a photocatalyst 50. As light contacts the photocatalyst 50, a mixture of ozone, superoxide, and hydroxyl radicals is released. To ensure a continuously desirable volume of ROS is produced by the photocatalyst, a set of nozzles 52 releases water vapor into the housing cavity to ensure that the air is at the proper humidity to maximize the production of ROS. The fan 44 continues to run, ensuring the airstream within the housing cavity is constantly mixing with the ROS that are produced by the corona discharge generator 46 and the ultraviolet light source emitting 185 nm wavelength light 48 in contact with the photocatalyst 50.

This pressurized air and ROS mixture encounter the pathogens on the surfaces and sub-surfaces of the objects or materials placed on the shelf, inactivating those pathogens. The longer the pressurized air and ROS mixture is circulated throughout the housing cavity, and the longer the ROS generators operate, the greater the pathogen inactivation rate. The time for contacting the contents within the housing 12 with the pressurized air and ROS mixture is specifically selected for the materials and objects to be treated by the apparatus.

Once the desired period has elapsed, the pathogen inactivation phase has ended, and the ROS decomposition phase begins. During this phase, the fan 44 continues to circulate the airstream and the heater 42 is switched on at a temperature between 50° C. and 100° C. Although ozone is more stable than related other ROS, its rate of decomposition will gradually increase with an increase in temperature between 20° C. and 100° C. At around 100° C. the rate of decomposition of ozone begins to rise at an accelerating rate with an increase in temperature, and at around 120° C., ozone rapidly decomposes to oxygen. Because some studies have shown that ozone can undergo explosive decomposition at around 105° C. at concentrations higher than 13%, heating of the airstream in the apparatus to facilitate decomposition of ozone is typically carried out at temperatures below 100° C.

During this heating phase, it is only necessary to heat the airstream to the selected temperatures because all the excess ROS is present in the airstream, and not on or in the objects and materials contained within the housing. A second ultraviolet light emitting source 54 having wavelengths between 240-315 nm and preferably at 254 nm is also switched on to facilitate further decomposition of ozone. The second ultraviolet light emitting source 54 also provides an additional benefit in that such wavelengths emitted are within the UVC spectrum and have a strong germicidal effect even in environments free of ROS.

The provision for the use of a second ultraviolet light emitting source 54 thus provides two functions; to decompose excess ROS remaining and continue to inactivate pathogens that may have survived the previous phase. As the airstream is exposed to the combination of heat at a temperature above 50° C. and the selected wavelengths of ultraviolet light, the ozone in the airstream begins to rapidly decompose into oxygen and water vapor.

After a period optimized for the decomposition of ozone, the heater 42 and the ultraviolet light emitting source 54 are switched off and the throttle valve 32 is engaged. The airstream is then propelled through a HEPA filter 58 as the pressures within the housing and the ambient environment begin to equalize. The HEPA filter 58 removes particles typically 0.3 microns and larger from the airstream. Because these larger airborne particulates are oftentimes colonized by much smaller pathogens, such as viruses, capturing the particulate matter in the HEPA filter 58 prevents the return of some of the inactivated pathogens or their residual components to the ambient air. At this point a high percentage of the pathogens in the airstream have been inactivated by the apparatus.

After passing through the HEPA filter 58, the airstream passes through the open throttle valve 32 and enters the activated carbon filter 34 where it reacts with ozone to produce oxygen, carbon dioxide and water vapor. The airstream continues to pass through activated carbon filter into the ozone destruction catalyst 36 which completes the removal of ozone to meet the ALARA (as low as reasonably achievable) threshold of less than 50 ppb ozone in the treated air that is emitted from the apparatus. With the fan 44 still engaged, the compressor 40 is started to draw fresh air from the environment to sweep through the housing and flow through the HEPA filter 58, the fully open throttle valve 32, and the ozone destruction catalyst 36 for a set period. The fan 44 is then switched off and the housing opened so that the disinfected objects and materials can be removed.

It is critical that the pathogens be exposed to the ROS for sufficient time and at a concentration that is high enough to allow the ROS to adequately inactivate the pathogens. As describe herein, the rate and effectiveness of a process to inactivate pathogens in biofilms and subsurface pores of materials and objects is increased by increasing the concentration of the ROS in contact with the pathogens. Similarly, the choice between the various ROS to be used in a pathogen inactivation device is dependent upon both the oxidation potential and stability of each individual ROS.

Radical ROS typically have higher oxidation potentials and higher reactivity but also much shorter half-lives compared to non-radical ROS. For example, at room temperature and in a clean vessel, the half-life of ozone may range from 20 to 100 hours in dry air. Comparatively, studies have shown that the half-life of a hydroxyl radical is around 1 nanosecond and the half-life of superoxide is around 5 seconds. While ozone is much more stable than a hydroxyl radical, it has a lower oxidation potential (2.07 v) than a hydroxyl radical (2.80 v). Rather than selecting one individual ROS based on stability or oxidation potential, the apparatus uses a mixture of highly reactive, short-lived ROS with less reactive but more stable ROS to inactive pathogens on the surfaces and in the sub-surface pores of objects and materials contaminated with biofilms.

Figure 4:
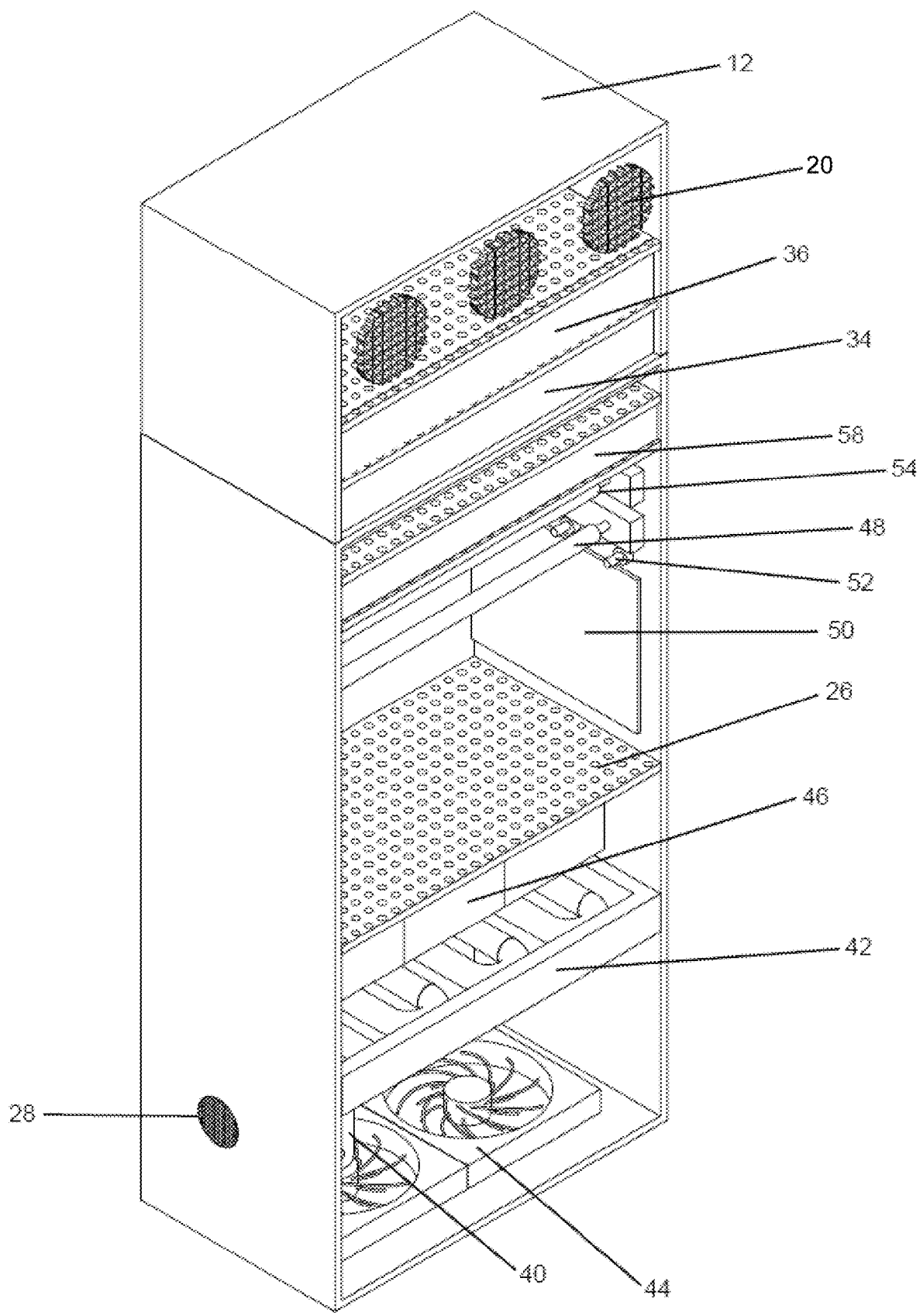
FIG. 4 illustrates a perspective view of an embodiment of the internal components for the apparatus for inactivation of airborne pathogens.

As seen in the perspective view of FIG. 4, the housing 12 is pressurized by turning on the compressor 40 to pull air through the air inlet 28 and into the housing cavity 30. The compressor 40 will typically be of a lower pressure, tankless variety capable of reaching pressure up to 4 atm in a small footprint. Next, throttle valve 32, as shown in FIG. 3, is closed to prevent air from escaping through the activated carbon filter 34, the ozone destruction catalyst 36, and the exhaust vent 20 while pressurizing the housing. The compressor 40 continues to run until the desired pressure is reached, between 1 to 4 atm but typically around 1.5 atm. As the pressure increases, the air within the housing cavity is forced deeper into the sub-surfaces of the materials and objects to be disinfected.

Figure 5:
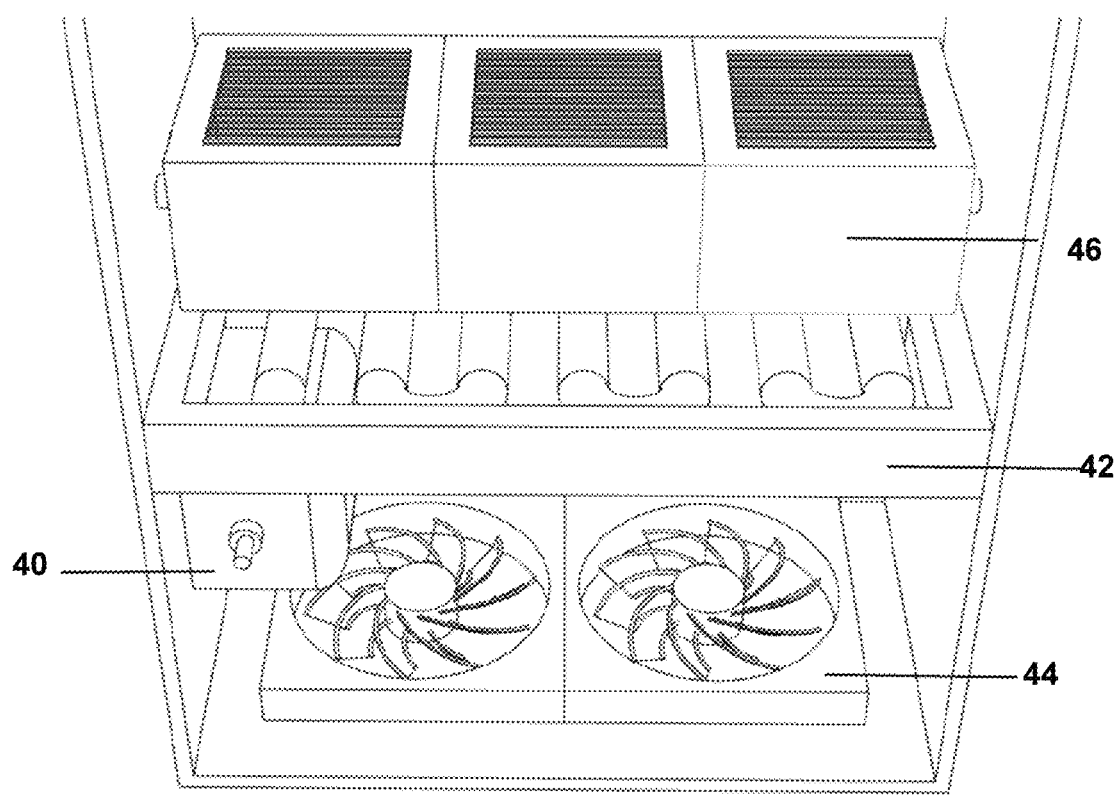
FIG. 5 illustrates a detailed perspective view of an embodiment of the lower section internal components for the apparatus for inactivation of airborne pathogens.

FIG. 5 shows an enhanced drawing of the bottom section of the apparatus. The fan 44 shown in the figure is a commercial fan typical of those used to move air throughout enclosed spaces and through conduits. The heater 42 consists of a heating element coil that converts electricity into radiant heat. This heater may be of any type of radiant heater that utilizes electricity to produce heat. The corona discharge generator 46 utilized may be any device capable of producing ozone and other ROS via the use of corona discharge. The corona discharge generator 46 can be a single device, or may be multiple corona discharge producing devices operating simultaneously. This will be dependent upon the size of the housing cavity, as a larger cavity can accommodate a larger corona discharge device or a larger number of corona discharge devices. Typically, the housing cavity is sized based on the size of the objects or materials that will need to be placed on the shelf within the cavity.

Figure 6:
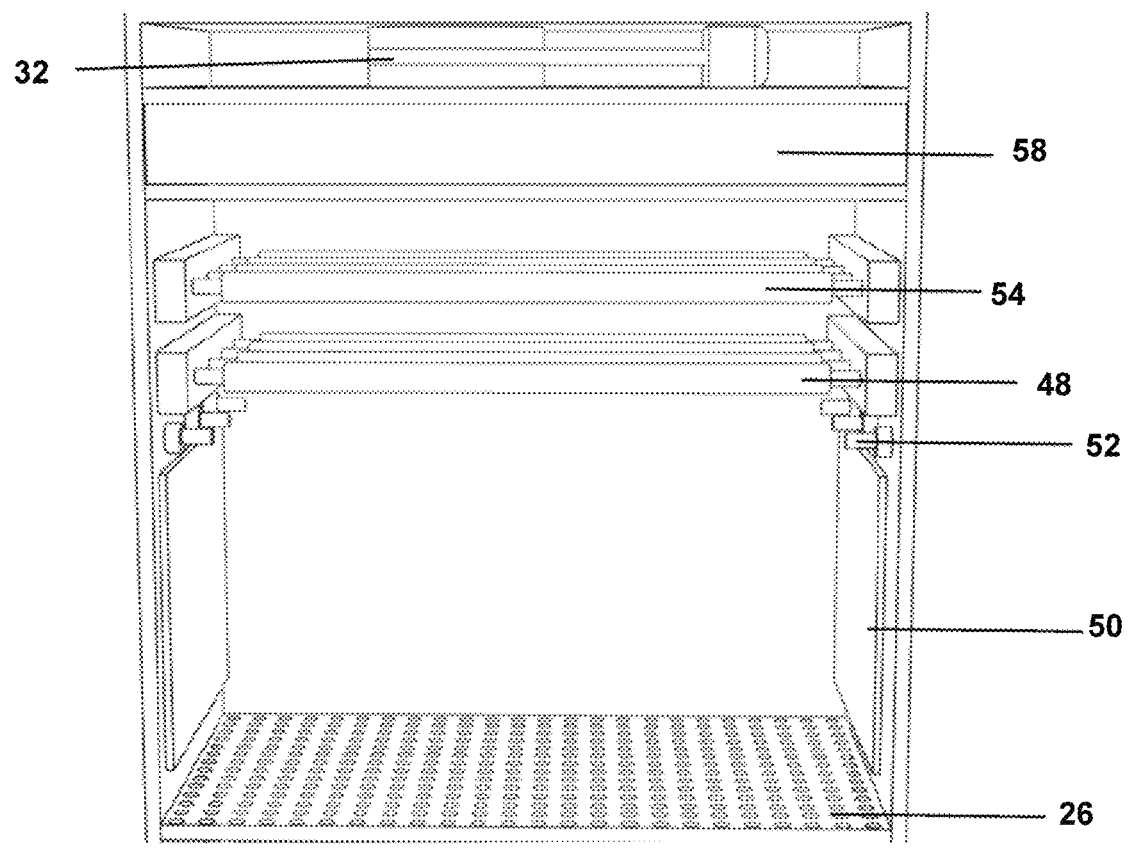
FIG. 6 illustrates a detailed perspective view of an embodiment of the middle section internal components for the apparatus for inactivation of airborne pathogens.

FIG. 6 shows an enhanced drawing of the middle section of the apparatus. The ultraviolet light emitting sources 48 and 54 will typically consist of a set LED lights emitting light at the desired wavelength. The photocatalyst 50 may be any photocatalyst capable of producing a mixture of ROS, but will typically be titanium dioxide. The number of ultraviolet sources, as well as the photocatalyst area 50, can be varied depending on the size of the housing cavity. This is like the corona discharge generator 46 as described above.

Figure 7:
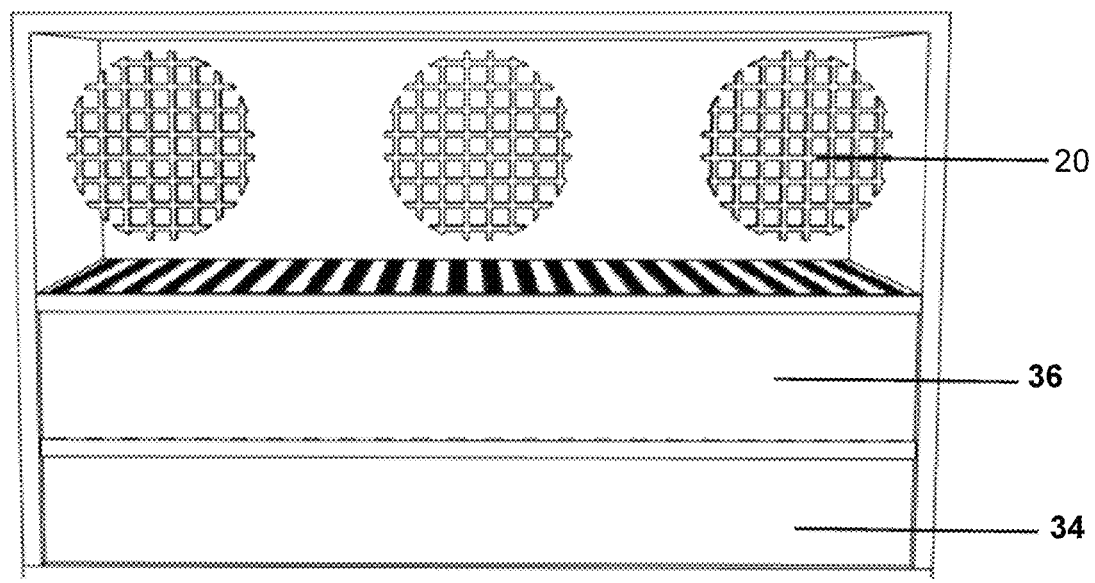
FIG. 7 illustrates a detailed perspective view of an embodiment of the top section internal components for the apparatus for inactivation of airborne pathogens.

FIG. 7 shows an enhanced drawing of the top section of the apparatus. The top section of the apparatus contains two major components—an activated carbon filter 34 and a fixture containing catalyst 36 that catalyzes the conversion of ROS into oxygen. The activated carbon filter 34 can be any manner of filter known to those skilled in the art including, an activated carbon block, activated carbon granules in a canister or activated carbon impregnated onto a substrate. The volume of the filter is sized in proportion to the airstream flow rate and space velocity. The ozone destruction catalyst 36 is designed to convert all ROS into oxygen and water vapor and which consists primarily of metal oxides impregnated upon various substrate supports. The construction and the composition of the ROS destruction catalyst and substrate are well known to those skilled in the art and are not described in detail herein.

Figure 8:
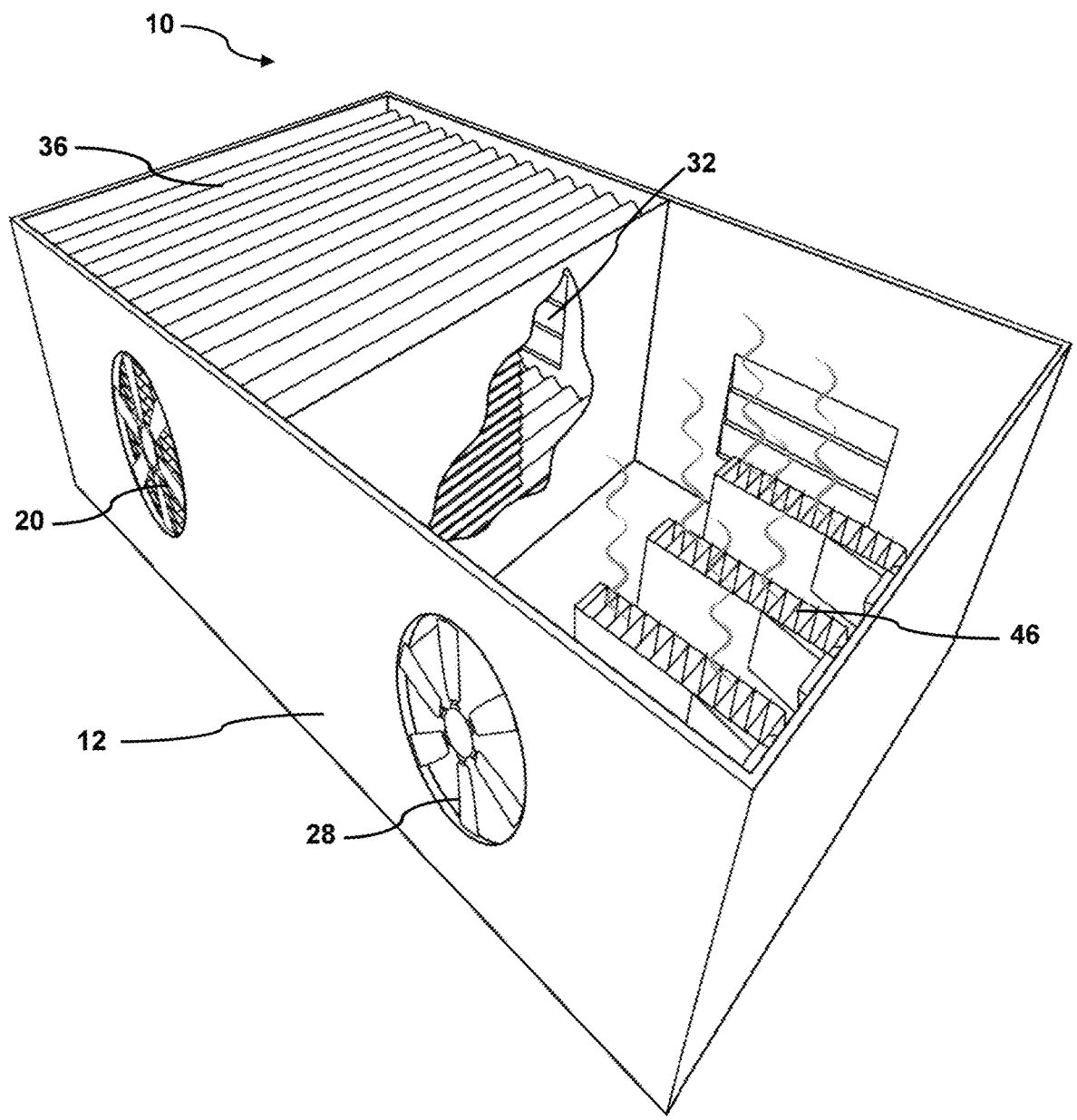
FIG. 8 illustrates a perspective view of an embodiment with side-by-side chambers for ozone creation and catalyst housing.

FIG. 8 details a perspective view of an embodiment of the apparatus 10 for inactivation of airborne pathogens and pathogens on the surface of an object. In this embodiment there are side-by-side chambers for ozone creation and catalyst housing. Operationally, air is pulled into the housing 12 by the air inlet fan 28 and traverses over the corona discharge generator 46. After pathogen inactivation, the airstream passes through the open throttle valve 32 and enters the ozone destruction catalyst 36 where it reacts to produce oxygen, carbon dioxide and water vapor to meet the ALARA (as low as reasonably achievable) threshold of less than 50 ppb ozone in the treated air that is emitted from the apparatus at the exhaust fan 20.

Figure 9:
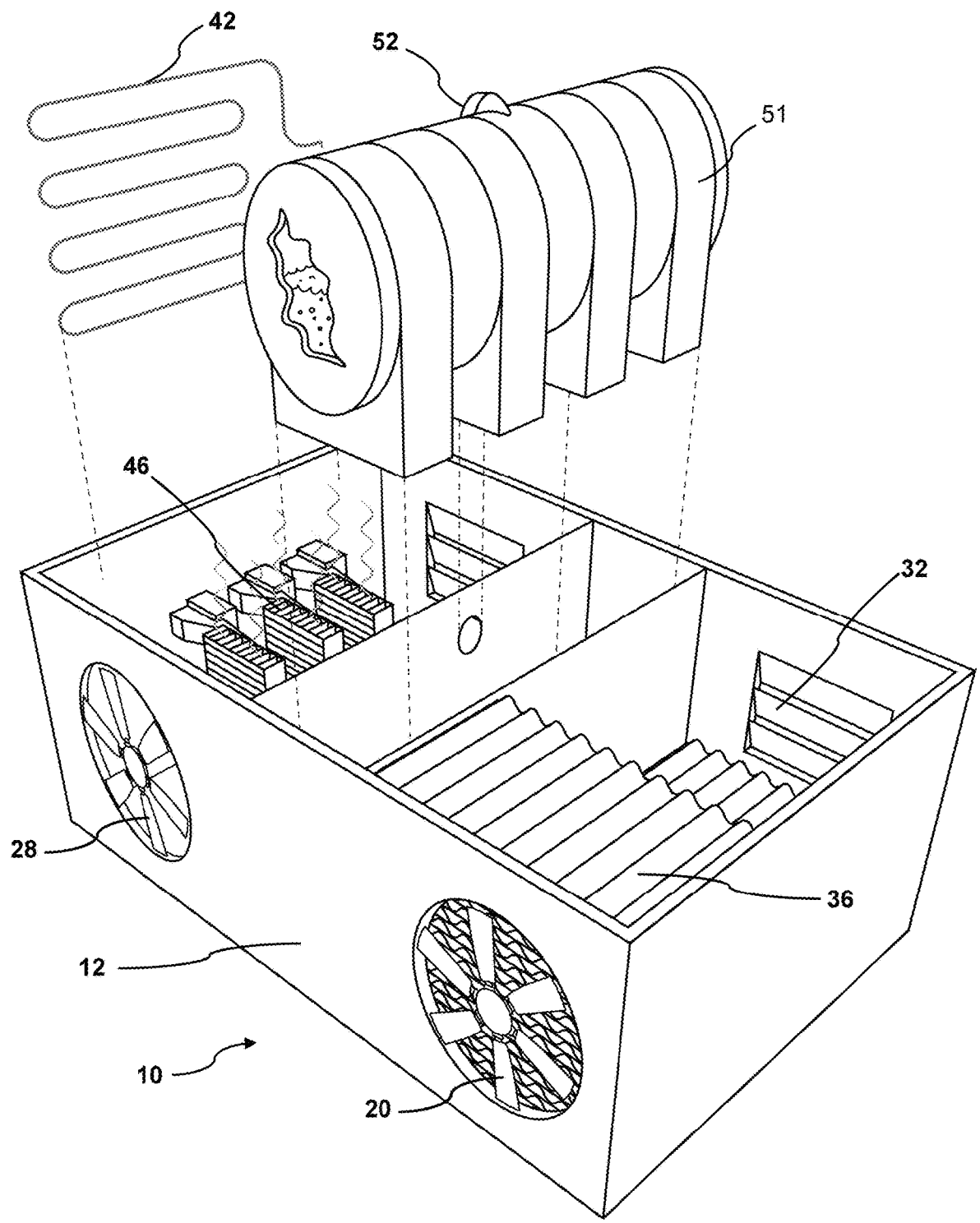
FIG. 9 illustrates a detailed perspective view of an embodiment with side-by-side chambers for ozone creation and catalyst housing with the ozone chamber including a heating element for elevating the temperature and a water tank for adding humidity to the ozone rich inlet air stream.

FIG. 9 illustrates an additional embodiment of the apparatus 10 for inactivation of airborne pathogens and pathogens on the surface of an object. This perspective view details the side-by-side chambers for ozone creation and catalyst housing with the ozone chamber including a heating element 42 for elevating the temperature and a water tank 51 with a set of spray nozzles 52 for adding humidity to the ozone rich inlet air stream.

Figure 10:
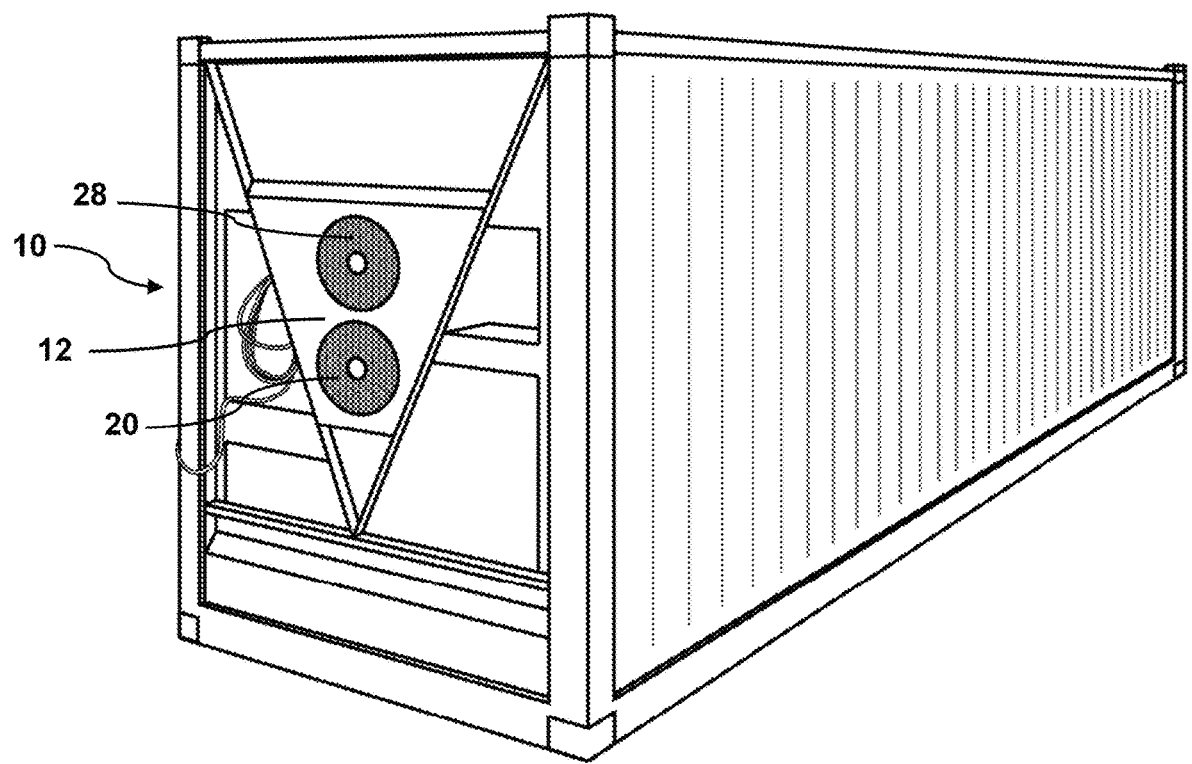
FIG. 10 illustrates a detailed perspective view of an embodiment for use with shipping containers.

FIG. 10 illustrates an additional embodiment of the apparatus 10 for use with shipping containers. The shipping container walls serving as the housing 12. FIG. 10 reveals that one of the longitudinally disposed ends of the shipping container housing 12 includes an air inlet vent 28 and an exhaust vent 20. An interior portion of the shipping container housing 12 is dedicated to the generation of ozone for use in inactivating the pathogens. A separate compartment, as detailed above, is utilized to convert the ROS to oxygen before being expelled to the ambient atmosphere at the exhaust vent 20.

Figure 11:
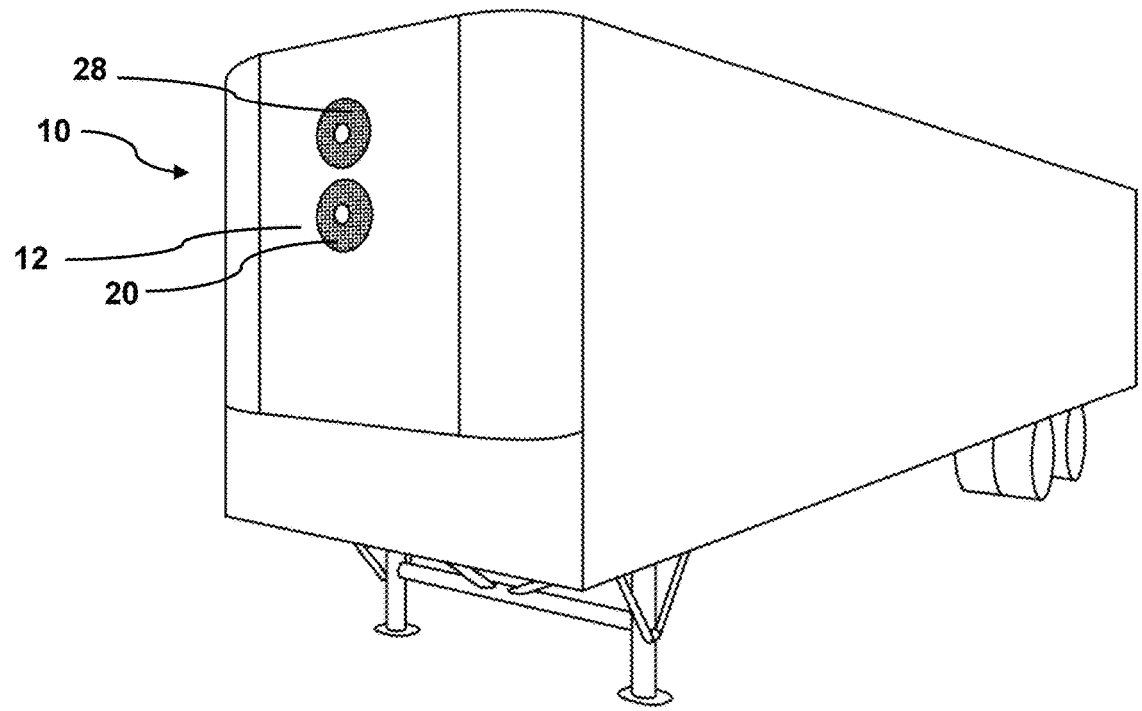
FIG. 11 illustrates a detailed perspective view of an embodiment for use with trailers.

FIG. 11 illustrates a detailed perspective view of an embodiment for use with trailers from a tractor-trailer combination. With an appearance much like a reefer trailer, the apparatus 10 for inactivation of airborne pathogens and pathogens on the surface of an object is disposed on the vertical wall of the trailer most closely spaced from the tractor in the position where a refrigeration unit is normally located. As seen in FIG. 11, the trailer mounted apparatus 10 includes a housing 12 as well as an ambient air inlet 28 and an exhaust vent/fan 20.

Figure 12:
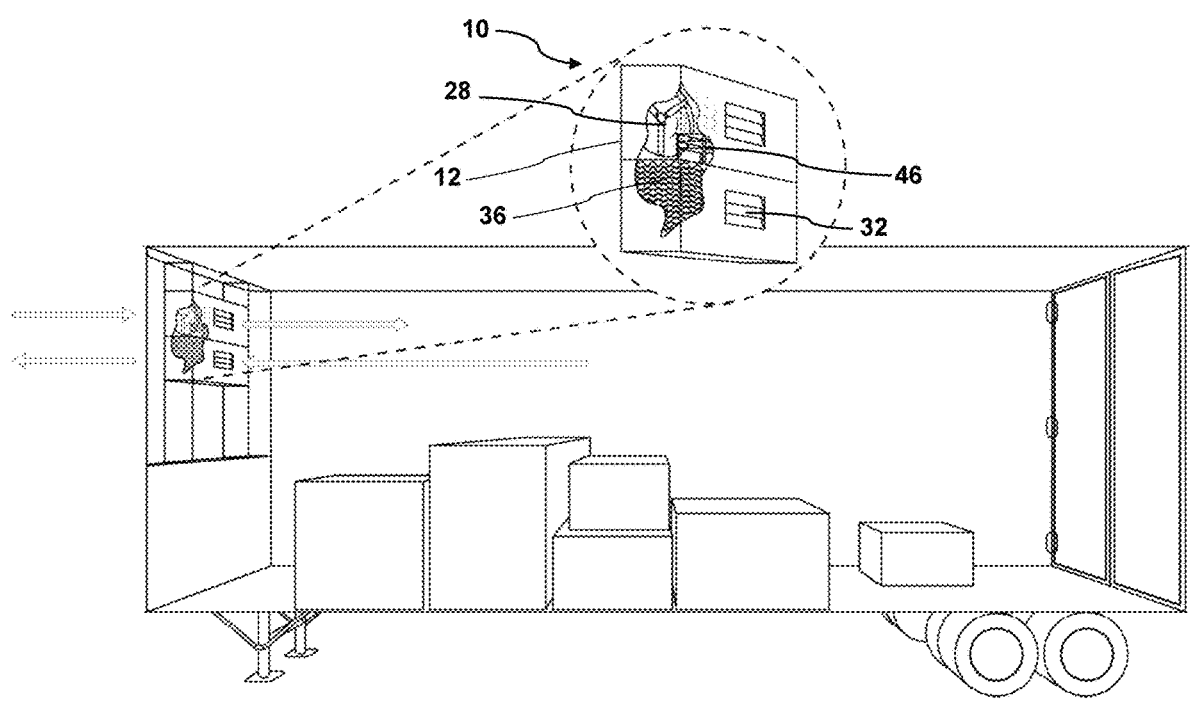
FIG. 12 illustrates a side view of an embodiment for use with trailers showing the apparatus in operation.

FIG. 12 depicts the interior space of a trailer loaded with boxes/packages that require inactivation of pathogens on the surface and possibly in the interior portions of the boxes/packages. The inactivation apparatus 10 as with the previously referenced embodiments utilizes a housing 12 providing an air inlet 28, a throttling valve 32, a corona discharge generator 46, and an ozone destruction catalyst 36.

Another embodiment (not shown) of the apparatus 10 for inactivation of airborne pathogens utilizes an aqueous oxidant instead of gaseous oxidant. An aqueous oxidant, such as hydrogen peroxide, is a strong oxidizer and is very effective in achieving pathogen inactivation. Studies have demonstrated that with aqueous oxidant significant pathogen inactivation can be achieved in short periods, ranging from 20 seconds to five minutes with an oxidant concentration of 0.1 mg/L to 4.68 mg/L. Disclosed herein is an embodiment of the apparatus for inactivation of airborne pathogens wherein the air stream is bathed in a reservoir of aqueous oxidant.

Any off-gassing of oxidant from the aqueous solution is removed through a reaction using a metallic catalyst, such as manganese dioxide as with the case for the use of the other ROS. Prior to the airflow passing through the manganese dioxide catalyst the air and airborne pathogens encounter a HEPA filter that captures particulates and pathogens colonized on the particulate matter that are larger than 0.3 microns. As previously indicated, those particles that are captured within the HEPA filter are continuously bathed in the oxidant and very likely inactivated so that upon removal and discarding of the HEPA filters there is a greatly diminished prospect of exposure to active pathogens.

In still another embodiment, the housing contains a rotating drum equipped with baffles into which the objects and materials to be disinfected are placed prior to being treated by the apparatus. The rotating drum maximizes contact between the pressurized mixture of air and oxidants and the enclosed materials and objects to be decontaminated while they are tumbled about during the inactivation stage of the process, and serves to fully expose the surfaces of such materials to the oxidants in the airstream and the ultraviolet radiation generated within the housing. This mode of operation with the rotating drum is especially suited for the treatment of "soft" materials consisting of clothing, bedding, masks, gowns, towels and the like.

In a final embodiment of the apparatus as disclosed herein, a reservoir containing water is used to contain water that is mechanically pumped into the airway path proximately the intake fan or air compressor to increase the relative humidity of the air. An appropriately sized spray nozzle or nozzles would be required to achieve the appropriate water droplet particle size. Studies have revealed that maximum anti-viral efficacy requires a short period of high humidity (>90% relative humidity) after the attainment of peak oxidant gas concentration (20-25 ppm). In the studies note above, all twelve viruses tested, on different hard and porous surfaces, and in the presence of biological fluids, could be inactivated by at least 3 log 10, in the laboratory and in simulated field trials. As has been extensively detailed above, the oxidant is subsequently decomposed to oxygen by a metallic catalyst prior to ejection at the exit area of the apparatus.

Any different arrangements of the various components depicted, as well as components not shown, are possible without departing from the spirit and scope of the disclosed technology. Embodiments of the disclosed technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosed technology.

It will be understood that certain features and sub combinations are of utility and may be employed without reference to other features and sub combinations and are contemplated within the scope of the claims. Not all steps listed in the various figures need be carried out in the specific order described.

We claim:

1. An apparatus for inactivation of airborne pathogens as well as pathogens resident on an object, the apparatus comprising:

a housing with an area for intake of air and an area for exhausting air and an airflow path disposed between the intake and exhaust areas;

a space within the housing for placement of the object, the space disposed between the intake and exhaust areas;

an intake fan;

an oxidant generator with a first end and a second end, the first end proximate the intake fan, the oxidant generator producing the oxidant to inactivate the airborne pathogens that are exposed to the oxidant;

a spiral shaped air channel baffle system proximate the first end of the oxidant generator, the baffle system for facilitating turbulent air flow to increase mixing of the generated oxidant and air;

at least one air filter disposed in the airflow path; and at least one of an activated carbon filter, and a catalyst to convert oxidant into oxygen, wherein the air and inactivated pathogens are discharged at the area for exhausting air.

2. An apparatus for inactivation of airborne pathogens and pathogens on the surface of an object, the apparatus comprising:

a housing with a cavity for intake of air and an area for exhausting air and an airflow path disposed between the intake and exhaust areas;

an area within the housing cavity for placement of the object, the area disposed between the intake area and the exhaust area;

an air compression apparatus for compressing intake air and increasing the air pressure within the cavity;

a receptacle with a bottom wall and at least one side wall, the receptacle containing an aqueous oxidant solution into which the compressed intake air is injected through at least one of the bottom wall, and the at least one side wall;

an air filter disposed in the airflow path;

at least one of an activated carbon filter, and a catalyst to convert oxidant into oxygen, wherein a portion of the air and inactivated pathogens are discharged at the area for exhausting air; and an enclosed airflow return loop configured to route a non-discharged portion of the air to an area proximate the first end of the oxidant generator.

3. The apparatus of claim 2, wherein a throttle valve is operable to prevent air from escaping through the activated carbon filter, the catalyst, and out through the exhaust area while the housing cavity is pressurized.

* * * * *